(12) United States Patent
Yerxa et al.

(10) Patent No.: US 7,247,623 B2
(45) Date of Patent: Jul. 24, 2007

(54) METHOD OF TREATING DRY EYE DISEASE WITH NON-DRYING ANTIHISTAMINES

(75) Inventors: Benjamin R. Yerxa, Raleigh, NC (US); Jason L. Vittitow, Durham, NC (US); John C. Ice, Jr., Wake Forest, NC (US)

(73) Assignee: Inspire Pharmaceuticals, Inc., Durham, NC (US)

( * ) Notice: Subject to any disclaimer, the term of this patent is extended or adjusted under 35 U.S.C. 154(b) by 0 days.

(21) Appl. No.: 11/503,029

(22) Filed: Aug. 10, 2006

(65) Prior Publication Data

US 2007/0043025 A1 Feb. 22, 2007

Related U.S. Application Data

(60) Provisional application No. 60/710,027, filed on Aug. 19, 2005.

(51) Int. Cl.
*A61K 31/55* (2006.01)
(52) U.S. Cl. .................... 514/214.02; 514/912
(58) Field of Classification Search .............. None
See application file for complete search history.

(56) References Cited

U.S. PATENT DOCUMENTS

| 4,313,931 | A | 2/1982 | Walther et al. ............... 424/45 |
| 4,753,945 | A | 6/1988 | Gilbard et al. ......... 514/263.31 |
| 4,868,154 | A | 9/1989 | Gilbard et al. ................ 514/13 |
| 5,668,133 | A | 9/1997 | Yanni et al. |
| 5,942,503 | A | 8/1999 | Jung et al. ............. 514/214.02 |
| 2002/0037297 | A1 | 3/2002 | Crespo et al. |
| 2004/0097486 | A1 | 5/2004 | Yanni .................... 514/217.05 |

OTHER PUBLICATIONS

Abelson et al., *Clinical Therapeutics*, vol. 26(1), 35-47, (2004).
Fugner et al., Arzneimittelforschung 38:1446-1453, (1988).
Ousler et al., *Ann Allergy Asthma Immunol.* 93:460-4, (2004).

*Primary Examiner*—Zohreh Fay
(74) *Attorney, Agent, or Firm*—Howrey LLP; Viola T. Kung

(57) ABSTRACT

A method and preparation for reducing dry eye symptoms and promoting tear secretion in a subject in need of such treatment is disclosed. The method comprises administering to the eyes of the subject a non-drying antihistamine compound, such as epinastine hydrochloride, in an amount effective to reduce dry eye symptoms and stimulate tear fluid secretion. Pharmaceutical formulations and methods of making the same are also disclosed. Methods of administering the compound include topical administration via a liquid, gel, cream, or as part of a contact lens or a continuous or selective release device; or systemic administration via nasal drops or spray, inhalation by nebulizer or other device, oral form (liquid or pill), injectable, intra-operative instillation or suppository form.

20 Claims, No Drawings

METHOD OF TREATING DRY EYE DISEASE WITH NON-DRYING ANTIHISTAMINES

This application claims the benefit of U.S. Provisional Application 60/710,027, filed Aug. 19, 2005, which is incorporated herein by reference in its entirety.

TECHNICAL FIELD

This invention relates to a method of reducing symptoms of ocular dryness in a subject. The method is useful in relieving dry eye symptoms, increasing tear secretion, and decreasing contact lens intolerance. The method involves administering to the subject in need thereof a non-drying antihistamine compound. The present invention is illustrated by epinastine hydrochloride.

BACKGROUND OF THE INVENTION

There are many situations where it is therapeutically desirable to increase the amount of tear fluid produced by the eye. Dry eye disease is the general term for indications produced by abnormalities of the precorneal tear film characterized by a decrease in tear production or an increase in tear film evaporation, together with the ocular surface disease and symptoms that result. Approximately 38 million Americans are affected with some type of dry eye disorder. Among the indications that are referred to by the general term "dry eye disease" are: keratoconjunctivitis sicca (KCS), age-related dry eye, Stevens-Johnson syndrome, Sjogren's syndrome, ocular cicatrical pemphigoid, blepharitis, corneal injury, infection, Riley-Day syndrome, congenital alacrima, nutritional disorders or deficiencies (including vitamins), pharmacologic side effects, contact lens intolerance, eye stress and glandular and tissue destruction, environmental exposure to smog, smoke, excessively dry air, airborne particulates, autoimmune and other immunodeficient disorders, and comatose patients rendered unable to blink.

Dry eye disease, although seen pathologically during ophthalmic exams as superficial punctate keratopathy (SPK) of the ocular surface epithelium, is largely a symptomatic disease. Chronic dryness leads to pain and irritation that is often debilitating to the subject, preventing the performance of normal daily activities such as reading, driving, etc. Dry eye is most common in postmenopausal women; however, hormone replacement therapy has not been proven to help dry eye signs and symptoms.

Currently, the pharmaceutical treatment of dry eye disease is mostly limited to administration of artificial tears (saline solution), anti-inflammatory agents (cyclosporine, steroids) and secretagogues (diquafosol, 15-HETE, rebamipide). In addition, artificial tears often have contraindications and incompatibility with soft contact lenses (M. Lemp, *Cornea* 9(1), S48-550 (1990)). The use of phosphodiesterase inhibitors, such as 3-isobutyl-1-methylxanthine (IBMX) to stimulate tear secretion is disclosed in U.S. Pat. No. 4,753,945. The effectiveness of these phosphodiesterase inhibitors has been investigated (J. Gilbard, et al., *Arch. Ophthal*, 112, 1614-16 (1994) and 109, 672-76 (1991); idem, *Inv. Ophthal. Vis. Sci.* 31, 1381-88 (1990)). Stimulation of tear secretion by topical application of melanocyte stimulating hormones is described in U.S. Pat. No. 4,868,154. Although these interventions can reduce inflammation and/or reduce SPK associated with dry eye, they have not been proven to significantly reduce the symptoms of dry eye.

U.S. Pat. No. 4,313,931 discloses a method of treating reactions provoked by liberation of histamine or serotonin; bronchial asthma; allergic bronchitis; allergic rhinitis; allergic conjunctivitis; or allergic diathesis in a warm-blooded host, which comprises administering to said host an effective amount of a fused dibenzo imidazolo compound such as epinastine.

U.S. Pat. No. 5,942,503 discloses a method for treating pain such as migraine, Bing-Horton syndrome, tension headache, muscular pain, inflammatory pain or neuralgias, in a patient in need thereof which comprises administering to said patient an analgesia producing amount of epinastine or a pharmaceutically acceptable salt thereof.

U.S. Pat. Publication No. 20040097486 discloses a method of treating vernal keratoconjunctivitis, giant papillary conjunctivitis, atopic keratoconjunctivitis, and allergic conjunctivitis in mammals, which comprises administering a composition comprising 0.01-0.3% of an $H_1$ antagonist and 0.05-1.5% of a safe steroid. Vernal keratoconjunctivitis is an allergic type of conjunctivis, which symptoms include severe ocular itching, and mild stringy, mucous discharge. Vernal keratoconjunctivitis is different from keratoconjunctivitis sicca, which is a dry eye disease. All the above cited U.S. Patents are incorporated herein by reference in their entirety.

Abelson, et al., have reported that epinastine reduces redness and itching associated with allergic conjunctivitis (M. B. *Clinical Therapeutics*, Vol. 26(1), 35-47, (2004)).

Ousler, et al. (*Ann Allergy Asthma Immunol.* 93:460-4, (2004)) reported that systemic antihistamines, such as loratadine and cetirizine hydrochloride, induced signs and symptoms associated with ocular dryness, including increased corneal and conjunctival staining, decreased TFBUT, and increased ocular discomfort in healthy individuals.

Dry eye disease is different from allergic conjunctivis; the two diseases have different patient populations. Dry eye symptoms are dryness, photophobia, foreign body sensation and grittiness in the eyes. Dry eye symptoms are different from the main complaint of itching associated with allergy, and are not related to histamine activity or allergic response. Redness of the eyes is not a main sign of dry eye disease. The primary end points for studying allergic conjunctivis are generally ocular itching and conjunctival hyperemia. The primary end points for studying dry eye diseases are corneal staining, tear volume (Schirmer tests), dryness, photophobia, foreign body sensation and grittiness.

As a result of the ineffectiveness and inconvenience of current therapies of dry eyes, there remains a need to provide a method for the treatment of dry eye disease, which is not only effective, but also free of significant side effects.

SUMMARY OF THE INVENTION

The present invention is directed to a method of reducing dry eye symptoms and stimulating tear secretion in a subject in need of such treatment. The method of the present invention can be used to reduce dry eye symptoms and increase tear production for any reason, including, but not limited to, treatment of dry eye disease. The method comprises the step of administering to the eyes of a subject in need thereof an effective amount of a non-drying antihistamine compound. A preferred method comprises topically administering a liquid or gel suspension of a non-drying antihistamine, such as epinastine hydrochloride, in an amount effective to reduce dry eye symptoms and to stimulate tear secretion.

The present invention is useful as a wash or irrigation solution to eyes of those who are unable to blink, for example, patients who cannot blink due to muscle or nerve damage, neuromuscular blockade or loss of the eyelids, comatose patients, or conscious individuals during surgery.

DETAILED DESCRIPTION OF THE INVENTION

The present invention is directed to a method of reducing dry eye symptoms such as dryness, photophobia, foreign body sensation and grittiness in a dry eye subject. The present invention is also directed to a method of stimulating tear secretion in a subject suffering from dry eye symptoms. The method comprises the step of first identifying a subject suffering from dry eye symptoms, then administering to the eyes of such subject an effective amount of a non-drying antihistamine compound.

Dry eye symptoms can be due to keratoconjunctivitis sicca (KCS), age-related dry eye, contact lens intolerance, Stevens-Johnson syndrome, Sjogren's syndrome, ocular cicatrical pemphigoid, blepharitis, corneal injury, infection, Riley-Day syndrome and congenital alacrima. Dry eye symptoms can also be caused by nutritional (such as vitamin) disorders or deficiencies, pharmacologic side effects, eye stress and glandular and tissue destruction, environmental exposure to smog, smoke, excessively dry air, airborne particulates, autoimmune and other immunodeficient disorders.

The present invention is also useful in reducing ocular symptoms associated with contact lens wear in a subject who develops contact lens intolerance due to dryness in the eyes. The method of the present invention can enhance the number of hours contact lens remains in the eye during the day, or can make wearing contact lens more comfortable to the user.

Applicants have discovered that non-drying antihistamines promote tear secretion and reduce symptoms of dry eye via HI receptor blockade on corneal nerves in the absence of an allergic response. The method of the present invention is an improvement upon the current most commonly used treatment of dry eye disease—artificial tears (i.e., saline solution), anti-inflammatory agents (cyclosporine), and secretagogues (15-HETE, and rebamipide). The method of the present invention stimulates a patient's own tear production and secretion, while providing analgesia of the symptomatic corneal irritation that occurs in dry eye. The method of the present invention has the benefit of acting as a topical analgesic in irritated eyes such as chronic dry eye and chronic contact lens wear with the added benefit of increased tear secretion.

The present invention is useful as a wash or irrigation solution to eyes of those who are unable to blink, for example, patients who cannot blink due to muscle or nerve damage, neuromuscular blockade or loss of the eyelids, comatose patients, or conscious individuals during surgery.

The term "non-drying antihistamine compounds," as used herein, are antihistamines and the pharmaceutically acceptable salts thereof that block $H_1$ receptors and do not have drying effects on the eyes as indicated by measuring tear volume. Non-drying antihistamine compounds generally do not have significant binding affinity for muscarinic receptors (e.g. $M_1$, $M_2$ and $M_3$) or do not have significant anticholinergic activities. Non-drying antihistamine compounds include epinastine, fexofenadine, emedastine, levocabastine, mequitazine, chlorpheniramine, brompheniramine, astemizole, terfenadine, rocastine, 5-[2-[4-bis(4-fluorophenyl)hydroxymethyl-1-piperid-inyl]ethyl]-3-methyl]-2-oxazolidinone ethanedioate, pyrilamine, clemastine, azelastine, ketotifen, and mapinastine. Preferred non-drying antihistamine compounds of this invention are epinastine and fexofenadine; with epinastine being further preferred.

Pharmaceutically acceptable salts are salts that retain the desired biological activity of the parent compound and do not impart undesired toxicological effects. Pharmaceutically acceptable salts include any addition salt with a pharmacologically acceptable acid as well as the free base. Examples of pharmaceutically acceptable salts are hydrochloride, hydrobromide, fumarate, acetate, etc.

Epinastine is the generic name of 3-amino-9,13b-dihydro-1H-dibenz[c,f]-imidazo[5,1-a]azepine. Epinastine hydrochloride was described by Fugner et al. (Arzneimittelforschung 38 (1988): 1446-1453). The active compound can be used in the form of a racemate or in the form of pure enantiomers or as a mixture of different proportions of both enantiomers. A common therapeutic salt for epinastine is hydrochloride. The invention described herein, however, is not limited to the hydrochloride but relates to any addition salt with a pharmacologically acceptable acid as well as the free base.

The present invention is concerned primarily with the treatment of human subjects, but can also be employed for the treatment of other mammalian subjects, such as dogs and cats, for veterinary purposes.

A preferred method of the present invention comprises topically administering a liquid or gel suspension of a non-drying antihistamine, such as epinastine hydrochloride, to the ocular surface of a subject, in an amount effective to reduce dry eye symptoms and to stimulate tear secretion.

The active compounds disclosed herein can be administered to the eyes of a patient by any suitable means, but are preferably administered as a liquid or gel suspension of the active compound in the form of drops, spray or gel. Alternatively, the active compounds can be applied to the eye via liposomes. Further, the active compounds can be infused into the tear film via a pump-catheter system. Another embodiment of the present invention involves the active compound contained within a continuous or selective-release device, for example, membranes such as, but not limited to, those employed in the Ocusert™ System (Alza Corp., Palo Alto, Calif.). As an additional embodiment, the active compounds can be contained within, carried by, or attached to contact lenses or other compatible controlled release materials, which are placed on the eye. Another embodiment of the present invention involves the active compound contained within a swab or sponge which can be applied to the ocular surface. Another embodiment of the present invention involves the active compound contained within a liquid spray which can be applied to the ocular surface. Another embodiment of the present invention involves an injection of the active compound directly into the lacrimal tissues or onto the eye surface.

The concentration of the active compound included in the topical solution is an amount sufficient to reduce dry eye symptoms and stimulate tear secretion. This solution is preferably an aqueous solution of a non-drying antihistamine compound and is in the range of 0.005-1.0%, preferably 0.01% to 0.1%, and most preferably about 0.05% (w/v). The preferred formulation includes a preservative, such as benzalkonium chloride (0.01% w/v) and inactive ingredients: edetate sodium, purified water, sodium chloride, sodium phosphate monobasic, sodium hydroxide and/or hydrochloric acid to adjust the pH to about 6-8, preferably about 7.

Depending upon the solubility of the particular formulation of active compound administered, the daily dose to reduce symptoms and promote tear secretion can be divided among one or several unit dose administrations. The total daily dose for epinastine, for example, can range from one drop (about 50 ill), one to four times a day, depending upon the age and condition of the subject. A currently preferred regimen for epinastine is one drop of 0.05% (w/v) solution, about 1 to 2 times a day.

The topical solution containing the active compound can also contain a physiologically compatible vehicle, as those skilled in the ophthalmic art can select using conventional criteria. The vehicles can be selected from the known ophthalmic vehicles which include, but are not limited to, saline solution, water polyethers such as polyethylene glycol, polyvinyls such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate and salts such as sodium chloride and potassium chloride.

In addition to the topical method of administration described above, there are various methods of administering the active compounds of the present invention systemically. One such method involves an aerosol suspension of respirable particles comprised of the active compound, which the subject inhales. The active compound is absorbed into the bloodstream via the lungs or contact the lacrimal tissues via nasolacrimal ducts, and subsequently contact the lacrimal glands in a pharmaceutically effective amount. The respirable particles can be liquid or solid, with a particle size sufficiently small to pass through the mouth and larynx upon inhalation; in general, particles ranging from about 1 to 10 microns, but more preferably 1-5 microns, in size are considered respirable.

Liquid pharmaceutical compositions of the active compound for producing a nasal spray or nasal or eye drops can be prepared by combining the active compound with a suitable vehicle, such as sterile pyrogen free water or sterile saline by techniques known to those skilled in the art.

Other method of systemic administration of the active compound involves oral administration, in which pharmaceutical compositions containing non-drying antihistamines, such as epinastine, are in the form of tablets, lozenges, aqueous or oily suspensions, dispersible powders or granules, emulsion, hard or soft capsules, or syrups or elixirs. Compositions intended for oral use can be prepared according to any method known to the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets. These excipients can be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets can be uncoated or they can be coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

A preferred systemic dosage form is oral administration. In a tablet, the preferred dose is 1-50 mg, preferably 5-25 mg and most preferably 10-20 mg of epinastine once or twice a day. Alternately, an oral syrup or dry syrup such as 1-2 teaspoons of a 1% (w/v) suspension once or twice a day can be administered.

Additional method of systemic administration of the active compound to the eyes of the subject involves a suppository form of the active compound, such that a therapeutically effective amount of the compound reaches the eyes via systemic absorption and circulation.

Further method of administration of the active compound involves direct intra-operative instillation of a gel, cream, powder, foam, crystal, liposomes, spray or liquid suspension form of said compound, such that a therapeutically effective amount of the compound reaches the eyes via systemic absorption and circulation.

The invention is illustrated further by the following examples which are not to be construed as limiting the invention in scope or spirit to the specific procedures described in it. An example in accordance with the invention was conducted on animals with dry eyes. It is recognized by those skilled in the art that results of ophthalmologic tests carried out in the aforementioned dry eye animal disease models have close correlation with humans afflicted with dry eye disease, and, therefore, the results provide an accurate prediction of therapeutic efficacy in humans.

EXAMPLES

Example 1

Effect of Topical Epinastine and Olopatadine on Tear Volume in Mice

Purpose

An in vivo example in accordance with the invention was conducted on an animal (mouse) model. The following example investigated the effects of topical epinastine and olopatadine ophthalmic solutions on tear volume in C57BL6 mice.

Methods

A total of 80 C57BL6 mice were divided into 3 treatment groups: epinastine ELESTAT®, Inspire, Durham, N.C.), olopatadine PATANOL®, Alcon, Ft. Worth, Tex.) and untreated controls. An additional group of 5 mice were treated with topical atropine 1% as an anticholinergic control. Mice in the epinastine, olopatadine and atropine groups had 1 µL of their respective drug instilled two times a day on the ocular surface. After two and four days of treatment, tear volume measurements were made with a phenol red impregnated cotton thread (Zone-Quick, Menicon, San Mateo, Calif.) 15, 45, 90, 120 and 240 min after the last instillation of the drug. A baseline tear measurement was performed before initiation of drug therapy. The untreated group had tear volume measurements done at the same time points. The length of tear wetting on the cotton thread was measured with a Nikon SMZ1500 microscope using Meta-Vue© software. A standard curve of cotton thread uptake was made using a glass micropipette with a known volume of a basic solution. Mouse tear volumes were calculated using regression analysis calculated by Microsoft® Excel. ANOVA with Tukey's Multiple Comparison Test was used for statistical analysis using GRAPHPAD PRISM™software.

Results

After 2 days of treatment, the epinastine-treated group showed higher mean tear volumes at 15, 45, 90 and 240 minutes than the olopatadine-treated group, reaching a statistically significant difference in tear volume at 45 min ($P<0.001$). The untreated group also had a statistically higher tear volume than the olopatadine group at 15 min ($P<0.05$) and 45 min ($P<0.05$). The epinastine-treated group showed an increased production of tears over the untreated group, but the difference was not statistically significant.

Similar results were found in tear volumes measured after 4 days of treatment; volumes were higher at all time points measured in the epinastine group, reaching a statistical significance over olopatadine at 45 min ($p<0.05$). The atropine-treated group showed no detectable tear volume at 15 min, 45 min and 90 min, but there was a return to baseline levels at 240 min.

CONCLUSIONS

The results indicate that olopatadine caused a significant decrease in tear volume, which could be due to the anticholinergic effects. Topical epinastine was not found to inhibit tear secretion, but rather increased tear production.

Example 2

Evaluation of the Ocular Drying Effect of Two Antihistamines: Topical Epinastine and Systemic Loratadine Purpose An in vivo example in accordance with the invention was conducted in human subjects. The following example investigated the effects of topical treatment with ELESTAT® (epinastine HCl ophthalmic solution, 0.05% w/v) and systemic treatment with loratadine, 10 mg, on parameters of ocular surface health, including tear production, tear flow and ocular surface staining.

Methods

Eighteen individuals completed a single-center, open label, four-visit, crossover study.

Visit 1 (Day 0): Baseline

Informed Consent was obtained; demographic data, medical history, and medication history were captured for consenting individuals. Baseline ophthalmic safety examinations were performed, including visual acuity and slit lamp biomicroscopy. Flourophotometry measurements were taken initially at time 0, then at time 1, 4, 7, 10, 13, 16, 19 minutes. The time 0 measurement was taken as a background fluorescence measurement. After background assessment, 1 µl of 2% unpreserved sodium fluorescein was instilled into the right eye of every subject throughout the study. Tear film break-up measurements and corneal and conjunctival staining were performed to further quantify ocular dryness. Tear film break-up time is a test of tear function. It is the time to the development of a dry spot on the cornea (i.e. break up of the pre-corneal tear film). Corneal and conjunctival staining are ways to measure ocular surface damage due to drying.

For the tear film break-up time (TFBUT) evaluations, 5 µl of 2% unpreserved sodium fluorescein was instilled into each eye. Corneal and conjunctival staining evaluations were performed using 5 µl of 2% unpreserved sodium fluorescein, instilled into each eye. The examiner waited one minute after instillation then began the evaluation and graded the three corneal regions and the two conjunctival regions. Corneal and conjunctival staining evaluations were also performed using 10 µl of 1% unpreserved lissamine green, instilled into each eye. The examiner graded the cornea (inferior, superior, and central) and conjunctiva (nasal and temporal) using a standardized scale from 0 to 4 points. Participants were then randomized to receive either oral loratadine 10 mg daily or ocular epinastine (ELESTAT®) 1 drop twice daily for the following 4 days.

Visit 2 (Day 4)

Medical and medication histories were updated, participants were queried about adverse events, and treatment compliance was evaluated. Tear volume and tear flow were evaluated via fluorophotometry. Ophthalmic examinations, including visual acuity, slit lamp biomicroscopy, TFBUT measurement, and corneal and conjunctival staining evaluations (using fluorescein and lissamine) were conducted. Subjects were instructed to refrain from the use of any other antihistamines and ophthalmic medications for 10 consecutive days.

There was no treatment after visit 2. This was a washout period to allow for the complete elimination of loratadine from systemic circulation.

Visit 3 (Day 14): Crossover

Medical and medication histories were updated, participants were queried about adverse events, and treatment compliance was evaluated. Tear volume, tear flow ophthalmic examinations (including visual acuity, slit lamp biomicroscopy, TFBUT measurement, and corneal and conjunctival staining evaluations) were conducted as before. Participants received the opposite medication from visit 1, followed by 4 days of treatment. Patients who received epinastine at visit 1 received loratadine and patients who received loratadine at visit 1 received epinastine.

Visit 4 (Day 18)

Medical and medication histories were updated, participants were queried about adverse events, and treatment compliance was evaluated. Tear volume, tear flow ophthalmic examinations were conducted as before.

Results

After 4 days of treatment, tear volume increased 7% in ELESTAT®-treated subjects compared to a 34% decrease in loratadine-treated subjects ($p=0.0357$). The ELESTAT®group also had a 10% increase in tear flow compared to a 35% decrease in the loratadine group ($p=0.0378$).

Similar results were seen with corneal and conjunctival staining. In ELESTAT®-treated participants, corneal and conjunctival staining decreased by 1%. Whereas in loratadine-treated participants, corneal and conjunctival staining increased by 22% ($p=0.0478$), which indicates an increase in ocular surface damage due to drying in loratadine-treated participants.

Although no significant change in TFBUT was observed after 4 days of treatment with loratadine, a trend was evident. Mean TFBUT decreased by 22% ($p=0.142$). In ELESTAT®-treated subjects, TFBUT decreased by less than 1%. The results again demonstrated that treatment with loratadine caused drying of the ocular surface whereas epinastine did not.

CONCLUSIONS

The above results indicate that epinastine increased both tear volume and tear flow after 4 days of treatment, while loratadine caused statistically significant decreases in both tear volume and tear flow. Additionally, ELESTAT® reduced corneal and conjunctival staining, while loratadine induced a statistically significant increase in staining. ELESTAT® also had no effect on tear film break-up time, while loratadine decreased TFBUT.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude this specification.

What is claimed is:

1. A method of treating dry eye disease in a subject, comprising the steps of first identifying a subject suffering from dry eye disease, then administering to the eyes of said subject an effective amount of 3-amino-9,13b-dihydro-1H-dibenz(c, f) imidazo (1, 5-a)azepine, or a pharmaceutically acceptable salt thereof.

2. The method according to claim 1, wherein said pharmaceutically acceptable salt is hydrochloride.

3. The method according to claim 1, wherein said method increases tear production.

4. The method according to claim 1, wherein said method reduces contact lens intolerance.

5. The method according to claim 1, wherein said effective amount is 0.01-0.1% (w/v).

6. The method according to claim 1, wherein said administration is topical administration of said compound to the ocular surface of the eyes.

7. The method according to claim 6, wherein said topical administration is administration of said compound via a carrier vehicle selected from the group consisting of drops of liquid, liquid wash, gels, ointments, sprays and liposomes.

8. The method according to claim 6, wherein said topical administration is infusion of said compound to said ocular surface via a device selected from the group consisting of a pump-catheter system, a continuous or selective release device, and a contact lens.

9. The method according to claim 1, wherein said administration is systemic administration.

10. The method according to claim 9, wherein said systemic administration is systemically administering a liquid or liquid suspension of said compound via nose drops, nasal spray, or nebulized liquid to nasopharyngeal airways of said subject, such that a therapeutically effective amount of said compound contacts the eyes of said subject via systemic absorption and circulation.

11. The method according to claim 9, wherein said systemic administration is administering an oral form of said compound, such that a therapeutically effective amount of said compound contacts the eyes of said subject via systemic absorption and circulation.

12. The method according to claim 9, wherein said systemic administration is administering an injectable form of said compound, such that a therapeutically effective amount of said compound contacts the lacrimal tissues of said subject via systemic absorption and circulation.

13. The method according to claim 9, wherein said systemic administration is administering a suppository form of said compound, such that a therapeutically effective amount of said compound contacts the eyes of said subject via systemic absorption and circulation.

14. The method according to claim 9, wherein said systemic administration is administering an intra-operative instillation of a gel, cream, powder, foam, crystal, liposome, spray or liquid suspension form of said compound, such that a therapeutically effective amount of said compound contacts the eyes of said subject via systemic absorption and circulation.

15. The method according to claim 1, wherein said compound is administered in an amount sufficient to achieve concentrations thereof on the ocular surfaces of said subject of from about $10^{-7}$ to about $10^{-1}$ moles/liter.

16. The method according to claim 2, wherein said effective amount is 0.01-0.1% (w/v).

17. The method according to claim 16, wherein said effective amount is about 0.05% (w/v).

18. The method according to claim 2, wherein said administration is topical administration of said compound to the ocular surface of the eyes.

19. The method according to claim 4, wherein said contact lens is soft contact lens.

20. The method according to claim 4, wherein said method enhances the number of hours a contact lens is tolerated in the eye.

* * * * *